Figure 1:
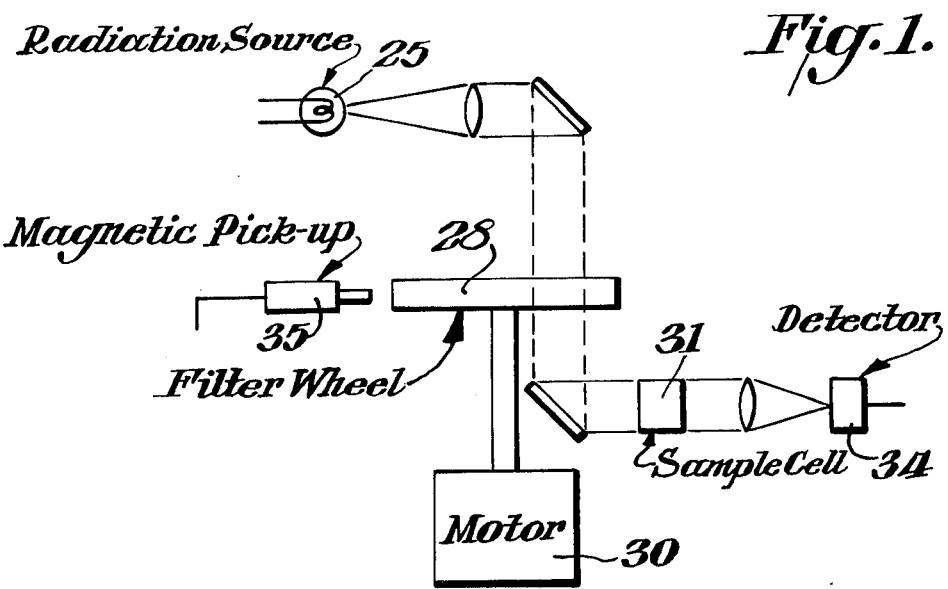

United States Patent [19]

Ida

[11] 4,076,424
[45] Feb. 28, 1978

[54] MULTI-CHANNEL IMPLICIT RATIO COMPUTER FOR SEQUENTIAL SIGNALS

[75] Inventor: Edward Stanley Ida, Newark, Del.

[73] Assignee: E. I. Du Pont de Nemours and Company, Wilmington, Del.

[21] Appl. No.: 670,080

[22] Filed: Mar. 24, 1976

[51] Int. Cl.² .................. G01J 3/48; G01N 21/22; H03K 5/18
[52] U.S. Cl. .................. 356/188; 250/565; 324/140 D; 328/161; 356/205
[58] Field of Search .................. 356/179, 188, 205; 250/565, 575; 324/140 D; 328/161

[56] References Cited

U.S. PATENT DOCUMENTS 3,955,096  5/1976  Faulhaber .................. 250/565

*Primary Examiner*—Vincent P. McGraw

[57] ABSTRACT

A multi-channel electrical signal ratioing circuit for a source delivering an electric analog pulse signal sequence having a broadened choice of ratio denominator terms provided by parallel-connected DC-coupled individual signal ratioing circuits each incorporating its own associated gated integrator, variable gain amplifier and at least one sampling circuit to form the several ratios needed. The basic ratioing circuit includes means for compensating against the effects of background influences, such as amplifier signal offsets, line voltage variations and changes in electrical system gains or other anomalies affecting ratio determination accuracy.

5 Claims, 6 Drawing Figures

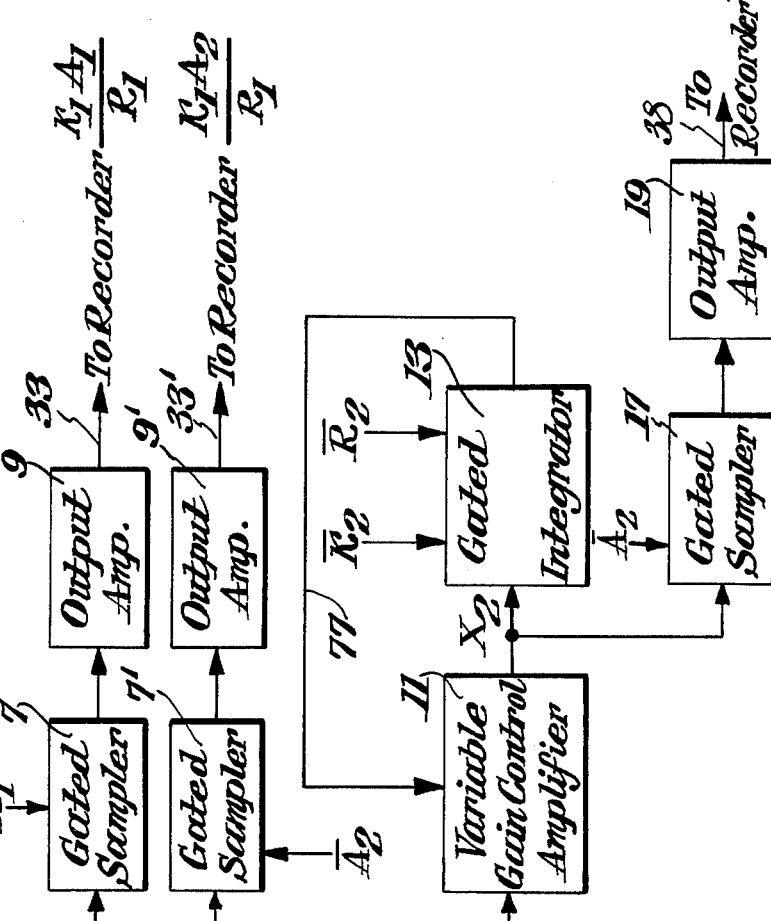
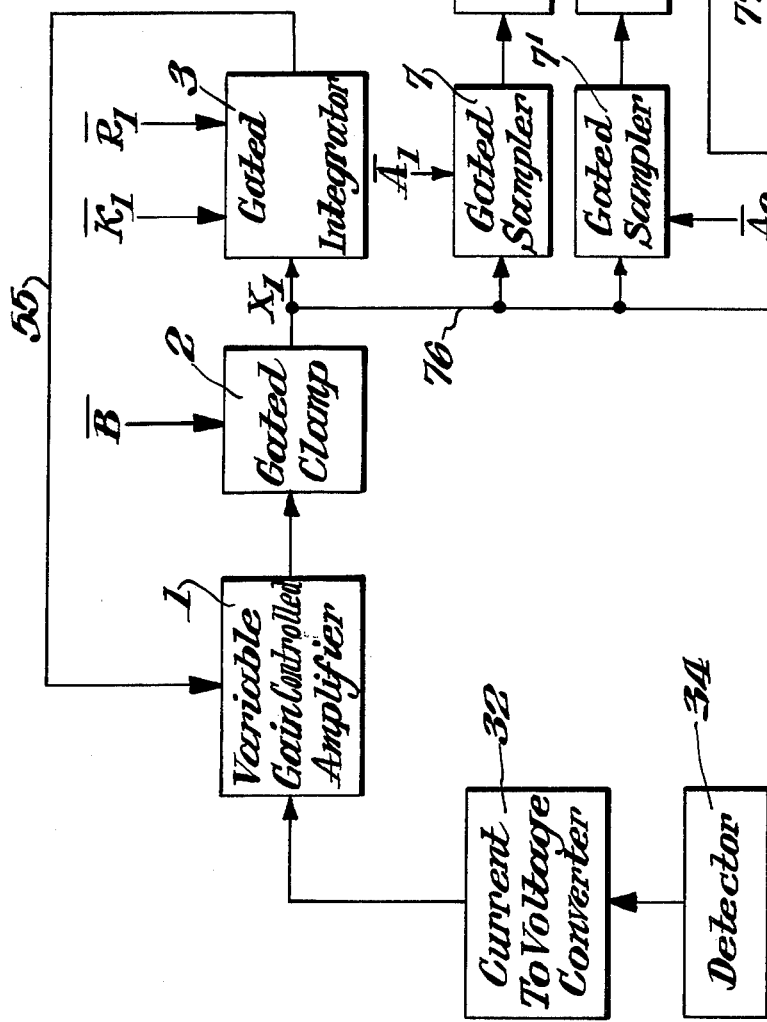

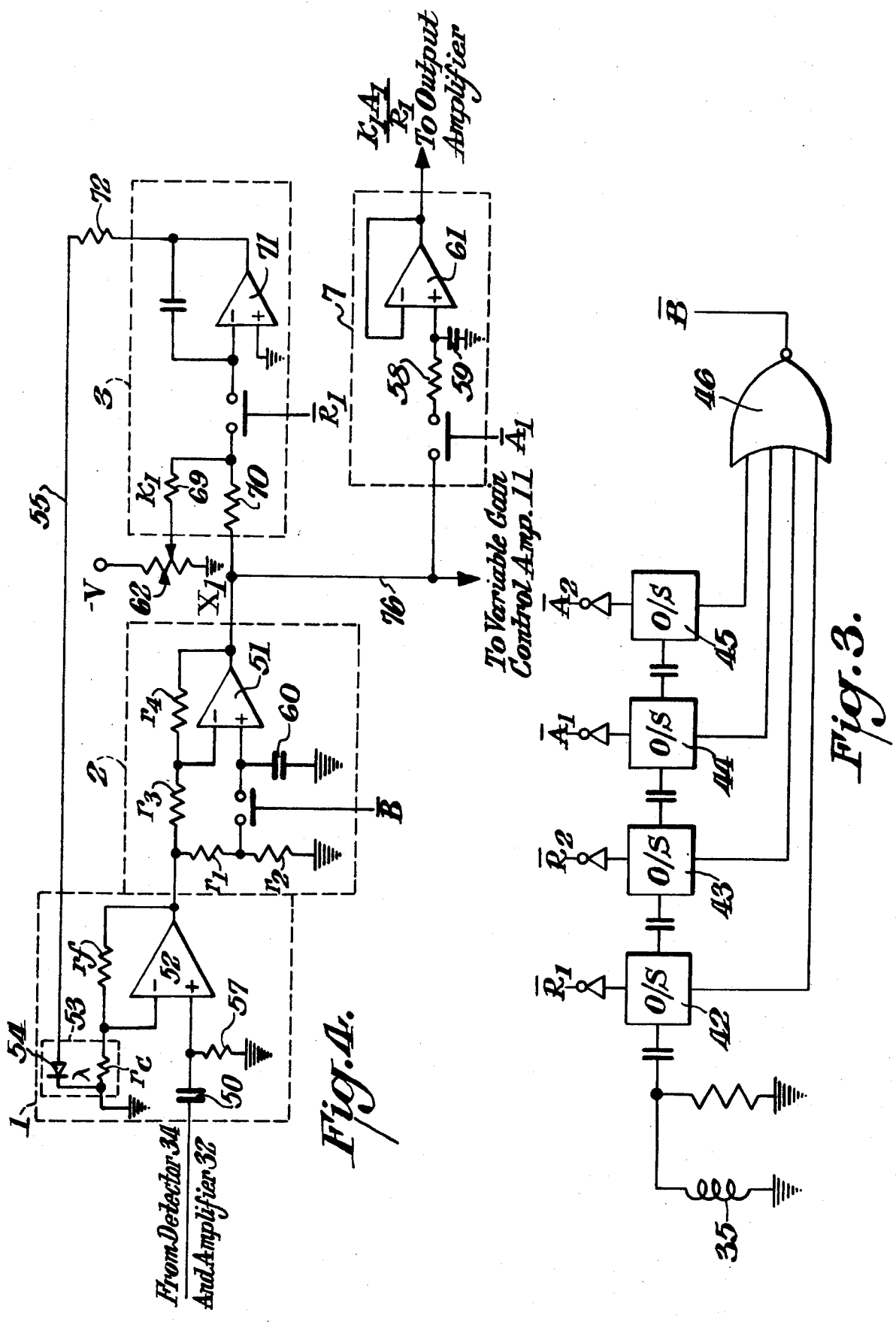

4,076,424

MULTI-CHANNEL IMPLICIT RATIO COMPUTER FOR SEQUENTIAL SIGNALS

RELATED PATENT APPLICATIONS

The invention of this application is an improvement on the "Implicit Ratio Computer for Sequential Signals" which is the subject of U.S. Pat. No. 3,955,096 issued May 4, 1976, and is described in utilization as the signal processor of a "Multiplex Optical Analyzer Apparatus" in patent application Ser. No. 670,079 cofiled on the same date herewith, both of which applications are of common assignment herewith.

BRIEF SUMMARY OF THE INVENTION

Generally, this invention relates to a multi-channel electrical signal ratioing circuit for a source delivering an electric analog signal pulse sequence constituting measured parameter signals $A_1, A_2, \ldots A_n$ and a plurality of reference signals $R_1, R_2 \ldots R_m$ comprising signal gating and timing means having signal identification means maintaining time coordination with the pulse sequence, and gate actuating means responsive to the signal identification means, actuating, for predetermined time durations, the respective gates corresponding to the parameter signals $A_1, A_2, \ldots A_n$ and the reference signals $R_1, R_2, \ldots R_m$, a first variable gain amplifier which imparts a gain G to the parameter and reference signals, a first gated integrator which, during a gated period $\bar{R}$, wherein at least one of reference signals $R_1, R_2, \ldots R_m$ is delivered, has a first input terminal receiving the sum of the signal pulse sequence of a given polarity from the first amplifier and a substantially constant preselected DC reference voltage K of opposite polarity, and a second input terminal connected to common, a feedback connection between the output side of the gated integrator and the first amplifier to control the gain-determining means thereof, a signal withdrawal circuit connection delivering the output of the first amplifier to a first sampling circuit incorporating at least one gated sampler and amplifier in parallel arrangement, each one reserved to the read-out of a predetermined one of the ratios $KA_1/R, KA_2/R, \ldots KA_n/R$ where R is the average of a selected set of reference signals admitted by the gated integrator during gated period $\bar{R}$, and additional individual ratioing channels, each incorporating its own variable gain amplifier, gated integrator feedback and gated sampler connected to the output of the first amplifier via the signal withdrawal circuit connection determining additional individual signal ratios with respect to other reference signal sets R selected from said plurality $R_1, R_2, \ldots R_m$.

DRAWINGS

Figure 1A:
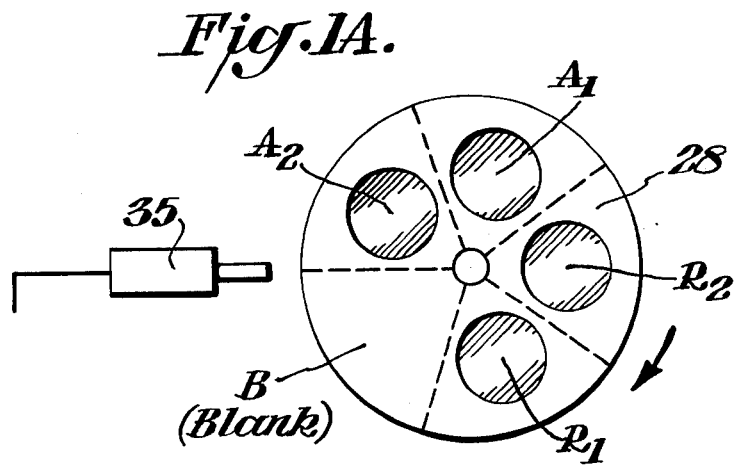

The following drawings constitute part of this specification, in which:

FIG. 1 is a schematic representation in side elevation of a photometric analyzer apparatus utilizing this invention, FIG. 1A is a plan view of a radiation filter wheel provided with circular filters which can be employed in the apparatus of FIG. 1, FIG. 2 is a block diagram of a preferred embodiment of the electrical circuitry of this invention, FIG. 2A is a schematic representation of a typical electric analog signal pulse sequence which constitutes the input processed by the apparatus of this invention, FIG. 3 is a schematic representation of gating and timing means utilized for the circuit of FIG. 2, and FIG. 4 is a schematic representation of the circuitry of the first channel of FIG. 2.

THE INVENTION

This invention comprises electrical circuitry for extracting information from an electric analog signal sequence which includes sequential data pulses, the information extracted being obtained as the ratio, or ratios, of combinations of these sequential pulses.

The invention is particularly useful for the processing of the output signal from a photodetector constituting part of a filter photometer, since it saves the expense of additional optical heads as well as complete individual electrical circuits for each such head. In addition, the present invention has the advantage of enhanced compactness.

Referring to FIG. 1, a typical design of photometer utilizes a radiation source 25 emitting radiation which, upon filtering, gives radiation wavelengths preferentially absorbed according to the Lambert-Beer Law by a multiplicity of components which it is desired to analyze, which are placed in, or flowed through, a radiation-transmitting sample cell 31. Transmitted radiation is transduced to electric analog signals by conventional photodetector 34. In this apparatus, a sequence of signals is obtained in regular time succession by a rotating filter wheel 28 which is driven at relatively high speed by motor 30. A magnetic pick-up 35, disposed at close clearance radially of filter wheel 28, generates a signal responsive to the circumferential passage of a small ferrous shim (not shown) mounted on the periphery of filter wheel 28, which coordinates, in time, circuit operation and gating with the successive interpositionings of the several radiation filters (and the blank sector) across the analytical radiation beam.

The objective of my invention is to obtain the ratios of signals such as $K_1A_1/R_1$ or $K_2A_2/R_2$ where $A_1$ and $A_2$ represent the measured parameter signals, as obtained, for example, as the electrically transduced values of analytical radiation transmitted to photodetector 34 such as via analytical radiation filters $A_1$ and $A_2$ of filter wheel 28, and $R_1$ and $R_2$ indicate the comparable values of the radiation passing through reference filters $R_1$ and $R_2$, while $K_1$ and $K_2$ denote generally constant multipliers, which may be unity.

The circuitry and operation of individual channels of my apparatus are practically identical with the invention of U.S. Pat. No. 3,955,096 supra and, therefore, the following description is condensed to the essentials, an infra-red radiation analyzer being chosen as the example.

First, it is necessary to eliminate the background contribution B, especially in infra-red region analyses, because $(A_1 + B)/(R + B) \neq A_1/R$. It is also desirable to compensate, or eliminate, optical and electronic system variations which do not represent true variations in the values of $A_1, A_2$ and R, examples of which are gain changes, e.g., dirt accumulations in the optics and line voltage variations or the existence of background, such as amplifier signal offsets and extraneous illumination.

Moreover, it is necessary to provide precise timing and gating facilities which permit processing each individual sequential data pulse of the train.

Referring to FIG. 2, in block diagram representation, the output of detector 34 is routed first to a current-to-voltage converter 32, then to a variable gain-controlled amplifier 1, then to gated clamp 2, the output of which is summed with a substantially constant d-c voltage $K_1$ of opposite polarity in gated integrator 3. The output signal of gated integrator 3 is utilized as feedback for gain-controlled amplifier 1, as hereinafter described.

In operation, the gains of amplifiers 32 and 1 in combination can be considered to have the value G. Then the sequential signals depicted in FIG. 2A have sequential components with amplitudes $G(R_1 + B)$, $G(R_2 + B)$, $G(A_1 + B)$, $G(A_2 + B)$, GB and so on in repetition of the scanning cycle.

The first essential is to eliminate the amplified background level GB, and this is accomplished in gated clamp 2 which subtracts the value GB from the entire signal, thereby effectively moving the zero base line to the position indicated by the broken horizontal lines in FIG. 2A.

The next operation on the signal is the subtraction of the reference voltage, $K_1$, from the $GR_1$ portion of the signal, followed by integration of the difference $(GR_1 - K_1)$ during the gated period in which reference $R_1$ occurs. This is accomplished by the gated integrator 3. The integrator output is employed as feedback to the gain-controlled amplifier 1, such that the average of the integrated values of $(GR_1 - K_1)$ over the time interval of the $R_1$ component of the pulse sequence is forced to equal zero. Expressed mathematically, when $$[\int_{t_1}^{t_2} (GR_1 - K_1) dt]_{avg.} = 0,$$

where $t_1$ and $t_2$ define the time period limits of the $R_1$ pulse, as shown in FIG. 2A, then $K_1 = GR_1$ or $G = K_1/R_1$, so that the combined action of the gated integrator 3 and the gated clamp 2 in the feedback configuration described produces an output signal at point $X_1$ in the loop which is in the sequence: $K_1$, $K_1R_2/R_1$, $K_1A_1/R_1$, $K_1A_2/R_1$, 0 and so forth in repetition of the cycle. Thus, the signal sequence as it exists at point $X_1$ is independent of gain changes, i.e., the effects of G, and is also devoid of background error, i.e., the effects of B. Moreover, the pulse sequence is now in useful ratio form modified only by the size of an arbitrary constant $K_1$, introduced as a fixed reference, which can have any preselected convenient value, including unity.

Referring again to FIG. 2, the signal at $X_1$ is analyzed by identical parallel sampling circuits, only two of which (determining $K_1A_1/R_1$ and $K_1A_2/R_1$) are shown in the drawing. The first is provided with a gated sampler 7 which is gated to sample the signal sequence for the duration of pulse $A_1$. There is thereby obtained an averaged value of the pulse which is amplified in output amplifier 9 to give a signal representative of the ratio $K_1A_1/R_1$ which can be passed to a voltmeter, recorder, or other output device (not shown) from terminal 33. Similarly, the second circuit branch is provided with gated sampler 7' which is gated to sample the signal sequence for the duration of the pulse $A_2$. There is thereby obtained an averaged value of the pulse which is routed to output amplifier 9', giving a representation of $K_1A_2/R_1$ which can be passed to a suitable output device (not shown) from terminal 33'.

Gating and timing pulses for actuation of gated clamp 2, gated integrator 3 and the gated samplers 7 and 7' can be provided by a number of conventional digital devices. One typical design can be that shown in block diagram in FIG. 3.

Here magnetic pick-up 35, disposed in peripheral proximity to the rotating filter wheel 28 in FIGS. 1 and 1A produces a triggering pulse once during each filter wheel rotation. This triggering pulse is routed to four "one-shots" in series, the first 42, producing a triggering pulse for sample period $\overline{R_1}$, which is supplied to gated integrator 3, as indicated by the distinctive notation in FIGS. 2, 3 and 4, where the bar above the pulse label symbolizes a gating period. After a suitable predetermined time delay, one-shot 42 triggers one-shot 43, thereby producing a triggering pulse $\overline{R_2}$ for reference $R_2$, which is applied to gated integrator 13. Then, after a suitable predetermined time delay, one-shot 43 triggers one-shot 44, thereby providing a triggering pulse for sample period $\overline{A_1}$, which is applied to gated sampler 7. Finally, again after a predetermined time delay, one-shot 44 triggers one-shot 45, thereby providing a triggering pulse for sample period $\overline{A_2}$, which, in this instance, is input to both gated sampler 7' and gated sampler 17 of the second channel, FIG. 2.

In those cases where more than one gated reference signal is needed to form a denominator term, the signal gating and timing means of FIG. 3 would be modified to include an OR gate (not shown) connecting the output pulses from the two reference sampling period one-shots $\overline{R_1}$ and $\overline{R_2}$ to the gated integrator.

Outputs are also taken from the one-shots 42, 43, 44 and 45 during their "on" periods which are supplied to NOR gate 46, so that, when no pulse is present on any of the four input lines to NOR gate 46, it produces an output pulse. This latter condition exists only during the period when the B sector (or opaque portion of the apertured filter wheel) is interposed in the optical path. Thus, the output pulse from NOR gate 46 then produces a triggering pulse for the sampling period B which is applied to gated clamp 2.

In a typical apparatus, filter wheel 28 is rotated at 1800 rpm, so that magnetic pick-up 35 pulses at about 33 millisecond time intervals. Thus, when the one-shots 42, 43, 44 and 45 are preset for a pulse length of about 6.6 ms, the circuit of FIG. 3 produces gating signals in proper synchronization with each filter wheel radiation type and also for the corresponding gated devices in the ratio computing circuit.

FIG. 4 is an electronic schematic drawing showing the principal components of one channel for an implicit ratioing circuit according to U.S. Pat. No. 3,955,096 supra constructed for processing the sequential output signals of an infra-red radiation spectrometer. The individual devices corresponding to the functional blocks of FIG. 2 are shown by enclosing broken line representation in FIG. 4.

In this design the sequential signal from detector 34, after transformation into a voltage signal in amplifier 32, FIG. 2, is capacitively coupled to variable gain-controlled amplifier 1 via capacitor 50, thereby eliminating the large bias value needed to operate detector 34 which is present in the analytical signal. Grounded resistor 57 is a voltage referencing (or maintaining) resistor. As hereinbefore described, the signal output from amplifier 1 has the successive magnitudes $G(R_1 + B)$, $G(R_2 + B)$, $G(A_1 + B)$, $G(A_2 + B)$, GB, etc. at the input of gated clamp 2.

When the GB pulse of the signal sequence occurs, the B gating signal from the circuit of FIG. 3 completes the circuit between the junction of the two resistors $r_1$ and $r_2$ (typically each 100 Kohm value) and capacitor 60 (typically 0.02 $\mu f$) connected between the positive input terminal of operational amplifier 51 and ground. Thus, with a signal level of GB appearing at the input, i.e., the junction of resistors $r_1$ and $r_3$ (typically each 100 Kohms) the signal level at the junction of resistors $r_1$ and $r_2$ will be ½ GB, and this voltage level is impressed on capacitor 60. For the signal level at point $X_1$ to be zero, the signal at the negative input terminal of operational amplifier 51 must also be ½ GB, and this will appear at the junction of the 100 Kohm resistors $r_3$ and $r_4$.

When the $\overline{B}$ gating signal ceases, at the end of the GB segment of the signal, the circuit between the junction of resistors $r_1$ and $r_2$ and the capacitor 60 opens, whereupon the voltage level of ½ GB is retained by capacitor 60 at the positive input terminal of amplifier 51, which thereupon continues to maintain a voltage of ½ GB at the negative input terminal. It is to be noted that there is essentially no signal level drop, because the only leakage path for capacitor 60 is through the extremely high impedance of amplifier 51.

Now, at the occurrence of the G($R_1$ + B), or $GR_1$ + GB, segment of the signal, there is no gating signal and the voltage level of ½ GB is still present at the positive and negative terminals of amplifier 51. Considering this composite signal, and evaluating the effect of the GB portion of this signal segment imposed at the input of the series equal-valued resistor pair $r_3$ and $r_4$, for the voltage ½ GB to appear at the junction of resistors $r_3$ and $r_4$, which is the negative input of amplifier 51, the voltage at $X_1$ must be zero. Then considering the $GR_1$ portion of this same composite signal segment, with a signal level of $GR_1$ imposed at the input point of resistor pair $r_3$ and $r_4$, and solving for the voltage at point $X_1$, the following is true: $GR_1$ + GB is input to $r_3$. Since ½ GB exists at the negative input of amplifier 51, the voltage drop across $r_3$ = ($GR_1$ + GB) − ½ GB. This equals the voltage drop across resistor $r_4$, which is ½ GB minus that existing at point $X_1$.

Therefore, solving for the voltage at $X_1$: ($GR_1$ + $GB$) − ½ $GB$ = ½ $GB$ − $X_1$ and, after simplifying, $X_1 = -GR_1$.

Thus, clamping a value of ½ GB at the positive input terminal of amplifier 51 effectively subtracts GB from each of the subsequent segments of the sequential signal, with the result that the successive background corrected signal outputs at point $X_1$ will be: $-GR_1$, $-GR_2$, $-GA_1$, $-GA_2$, 0, etc. The recurrent $-GR_1$ signal values are, of course, those used by the gated integrator 3 to produce feedback voltage values to variable gain-controlled amplifier 1.

Referring again to FIG. 4, the output of amplifier 52 is fed back to its negative input terminal through resistor $r_f$, which is also connected to ground through the light-sensitive resistor $r_c$, which is part of the light feedback component 53 (typically a Clairex "Photomod" CLM 6000 which combines, in a single radiation-tight housing, the light-emitting diode 54 with $r_c$). The resistance of $r_c$ varies inversely with the intensity of the radiation impinging on it from diode 54, resistance values changing, typically, several orders of magnitude in range from light to dark. The gain of amplifier 52 in this configuration is (1 + $r_f/r_c$).

In operation, if the gain of amplifier 32 (FIG. 2) decreases slightly, then the amplitudes of all of the signal pulses (FIG. 2A) become proportionately smaller. In this event, when the reference gate signal $\overline{R_1}$ switches integrator 3 on, a smaller value, $G'R_1$, will be combined with $K_1$ for integration. Then, in a manner previously mentioned, since this $G'R_1$ no longer equals $K_1$, the resulting difference is integrated to produce a new feedback signal which, via line 55, increases the light output of diode 54 in the radiation feedback component 53. This, in turn, decreases the resistance of $r_c$, which thereupon increases the gain of amplifier 52. This increase continues until the time average value of $$\int_{t_1}^{t_2} (G'R_1 - K_1) dt$$

forced to equal 0. Thus, not only is gain stabilization achieved, but there is also obtained the ratioing function desired. It might be mentioned that 62 is a voltage selection potentiometer, resistors 69 and 70 are current summing resistors, amplifier 71 is an operational amplifier connected as an integrator and resistor 72 is a current-limiting resistor for diode 54.

The particular light feedback arrangement shown for gain-controlled amplifier 1 was chosen from several alternate positions of light-sensitive resistor $r_c$ in the feedback input-output circuit. The arrangement described is preferred, because it provides a high, constant input impedance and a quasi-linear control function for the gain of the operational amplifier 52.

The individual signal sampling circuits 7 and 7' (FIG. 2) are identical, each being gated by its applicable parameter gated signal $\overline{A_1}$ or $\overline{A_2}$ as denoted.

Describing only one gated sampler 7, FIG. 4, there is provided a resistor 58-capacitor 59 combination to effect averaging of the input signal. In addition, capacitor 59 retains the average amplitude of the signal, so that a $K_1A_1/R_1$ signal is held throughout the full signal sequence cycle. The output signal from amplifier 61 is $K_1A_1/R_1$ which is passed to a conventional output amplifier, not shown.

The instant invention affords means to obtain two or more ratios, each having different denominator terms, e.g., reference radiation values $R_1$ and $R_2$, selected from arbitrary locations within a recurrent time sequential input signal pulse train such as shown in FIG. 2A. Accordingly, there are provided two or more ratioing channels, each incorporating essentially the implicit ratio circuits of the design taught in U.S. Pat. No. 3,955,096 hereinbefore described, where a resistance has been used to replace the coupling capacitance 50 of FIG. 4 connected and gated so that the output pulse train produced by the first gain-controlled amplifier 1, having a gain $G_1 = K_1/R_1$, is used as input signal to a second gain-controlled amplifier having a gain $G_2 = K_2/R_2$ to form an output signal based exclusively on a second reference value $R_2$. In FIG. 2 one such added channel is shown, in which the variable gain-controlled amplifier is denoted 11 whereas the associated gated integrator is 13, and the output signal is withdrawn from intermediate point $X_2$ connected to a signal sampling sub-circuit provided with gated sampler 17.

This arrangement is especially useful in the field of spectrophotometry, where a single instrument can be used to analyze the concentration of several constituents within a process stream (or streams) based on independent reference values $R_1$ and $R_2$.

Referring to FIG. 2, the arrangement of the two implicit ratioing channels detailed is such that the first channel computes the ratios $K_1A_1/R_1$ and $K_1A_2/R_1$ as hereinbefore described, whereas the second channel computes the ratio $K_2A_2/R_2$, the latter two ratios being essential to photometric analyses of two samples constituents based on separate references which are completely independent of one another. To obtain the ratio $K_2A_2/R_2$, ratio signal $K_1A_2/R_1$ is input to the second channel via signal withdrawal circuit connection 76 connected to point $X_1$ and then gated during sampling period $A_2$. As hereinafter described, variations in system gain produced by the first variable gain amplifier 1 have no effect on the values of the ratio signals measured at the output of the second variable gain-controlled amplifier 11.

In operation, the succession of signals appearing at point $X_1$ will be as follows: $K_1$, $K_1R_2/R_1$, $K_1A_1/R_1$, $K_1A_2/R_1$, 0, etc., the cycle then repeating itself.

Upon processing by variable gain-controlled amplifier 11, the output sequence therefrom is, at first, $G_2K_1$, $G_2K_1R_2/R_1$, $G_2K_1A_1/R_1$, $G_2K_1A_2/R_1$, 0, etc., where $G_2$ is the gain of amplifier 11. Gated integrator 13 has a DC input of $K_2$ and, upon being gated for reference interval $\overline{R_2}$, produces a feedback signal fed back to amplifier 11 via feedback connection 77. Again, the feedback of interest is dependent upon the integral of the difference between $K_2$ and $G_2R_2$, expressed mathematically as $$\left[ \int_{t_2}^{t_3} \left( \frac{G_2K_1R_2}{R_1} - K_2 \right) dt \right]_{avg.} = 0.$$

When the integral expression is forced to equal zero, $G_2 = K_2R_1/K_1R_2$ with the result that the signal sequence at point $X_2$ becomes $K_2R_1/R_2$, $K_2$, $K_2A_1/R_2$, $K_2A_2/R_2$, 0, etc., repeating cyclically. It is apparent from this that all input signals through variable gain-controlled amplifier 11 are now referred to a new base, $R_2$.

With the $\overline{A_2}$ logic signal applied to gated sampler 17, the $K_2A_2/R_2$ pulse is selected and routed through output amplifier 19, from which it can be passed, via line 38, to a recorder or other desired instrument. It is apparent that the output from amplifier 19 is independent of not only $G_1$ but also $G_2$ and $K_1$ as well.

In a similar manner, additional channels of implicit ratioing circuitry can be added with input terminals of each succeeding variable gain-controlled amplifier connected to point $X_1$ to provide additional ratioing capability. Connection point $X_1$ is usually preferred to avoid any offset which may be introduced into the signal by a preceding amplifier. However, if this is no problem, succeeding inputs for subsequent variable gain-controlled amplifiers can be equally well withdrawn from the corresponding points $X_2$, $X_3$, ... $X_n$ of each preceding channel in turn.

In photometric analysis it is often preferred to work with the logarithms of the ratios computed, and this is effected simply by merely interposing logarithmic amplifiers between each gated sampler, e.g., 7, 7' and 17 of FIG. 2, and its associated output amplifier 9, 9' and 19, respectively.

Gated clamp 2 can be dispensed with where relatively large amplitude signal sequences, with respect to any offset introduced by the amplifier, are received from photodetector 34; however, when relatively weak signals are processed, as in photometric analysis, such a clamp is advantageous. However, unless the input terminals of the succeeding variable gain amplifiers are direct-coupled to signal withdrawal points $X_1$ or $X_2$, i.e., by replacing coupling capacitance 50 of FIG. 4 with a resistor, each ratioing stage must include a gated clamp to nullify the associated offset introduced by each coupling capacitance.

What is claimed is:

1. In a multi-channel electrical signal ratioing circuit for a source delivering an electric analog signal pulse sequence constituting measured parameter signals $A_1$, $A_2$ ... $A_n$ and a plurality of reference signals $R_1$, $R_2$ ... $R_m$, signal gating and timing means having signal identification means maintaining time coordination with said signal pulse sequence, and gate actuating means responsive to said signal identification means, actuating, for predetermined time durations, the respective gates corresponding to said parameter signals $A_1$, $A_2$ ... $A_n$, and said reference signals $R_1$, $R_2$ ... $R_m$, a first variable gain amplifier which imparts a gain G to said parameter and reference signals, a first gated integrator which, during a gated period $\overline{R}$, wherein at least one of said reference signals $R_1$, $R_2$ ... $R_m$ is delivered, has a first input terminal receiving the sum of said signal pulse sequence of a given polarity from said amplifier and a substantially constant preselected DC reference voltage K of opposite polarity, and a second input terminal connected to common, a feedback connection between the output side of said gated integrator and said first amplifier to control the gain-determining means thereof, a signal withdrawal circuit connection delivering said output of said first amplifier to a first sampling circuit incorporating at least one gated sampler reserved to the readout of a preselected one of the ratios $KA_1/R$, $KA_2/R$, ... $KA_n/R$, where R is the time average of a selected set of reference signals admitted by the gated integrator during said gated period $\overline{R}$, and additional individual ratioing channels, each incorporating its own variable gain amplifier, gated integrator feedback and sampling circuit, connected to the output of said first amplifier via said signal withdrawal circuit connection determining additional signal ratios with respect to other reference signal sets R selected from said plurality $R_1$, $R_2$ ... $R_m$.

2. In a multi-channel electrical signal ratioing circuit according to claim 1, wherein said electric analog signal pulse sequence includes a background signal B, the improvement comprising a gated clamp interposed between the output side of said first variable gain amplifier and said signal withdrawal circuit connection delivering said output of said first amplifier to said sampling circuit and said additional ratioing channels.

3. A multi-channel electrical signal ratioing circuit according to claim 1 wherein each said additional individual ratioing channel withdraws its signal input from the output side of said variable gain amplifier in the immediately preceding one of said individual ratioing channels.

4. The multi-channel electrical signal ratioing circuit of claim 1 wherein said electric analog pulse sequence is the output of a filter photometer.

5. The multi-channel electrical signal ratioing circuit of claim 2 wherein said electric analog pulse sequence is the output of a filter photometer.

* * * * *